United States Patent [19]

Leka

[11] Patent Number: 5,411,657
[45] Date of Patent: May 2, 1995

[54] MOLDED PLASTIC ELECTROPHORESIS CASSETTES

[76] Inventor: George T. Leka, 4444 Madison Ave., Trumbull, Conn. 06611

[21] Appl. No.: 121,601

[22] Filed: Sep. 14, 1993

[51] Int. Cl.⁶ .................... G01N 27/26; G01N 27/447
[52] U.S. Cl. ............................. 204/299 R; 204/182.8
[58] Field of Search ......................... 204/299 R, 182.8

[56] References Cited

U.S. PATENT DOCUMENTS 4,119,521  10/1978  Chirikjian ...................... 204/299 R

OTHER PUBLICATIONS

Robert O. Poyton "A Versatile Apparatus for Polyacrylamide and Agarose Gel Electrophoresis in Plexiglass Slab Gel Molds" Analytical Bochemistry, vol. 90, No. 2 (Oct. 15, 1978) 624–632.

*Primary Examiner*—John Niebling
*Assistant Examiner*—John S. Starsiak, Jr.
*Attorney, Agent, or Firm*—John R. Doherty

[57] ABSTRACT

An electrophoresis cassette is provided including a thin, flat, rectangular, molded plastic front plate which overlies a thin, flat, rectangular, molded plastic back plate in opposing spaced apart relationship, the front and back plates being separated from each other by a thin, narrow, generally U-shaped embossment formed on the opposing surface of the back plate and extending along the two opposite side edges and the bottom edge of the back plate. A liquid-tight seal formed by an ultrasonic weld extends continuously along the embossment and joins the plates together, the plates defining therebetween a narrow gap for holding a gel medium. An elongated narrow groove is provided within the non-opposing surface of each plate and extends in substantially coinciding relation with the groove in the other plate across the bottom of the plates at a point just above the seal, the grooves forming at the bottom portion of the cassette a tab which can be easily broken off to expose the gel medium within the gap.

15 Claims, 5 Drawing Sheets

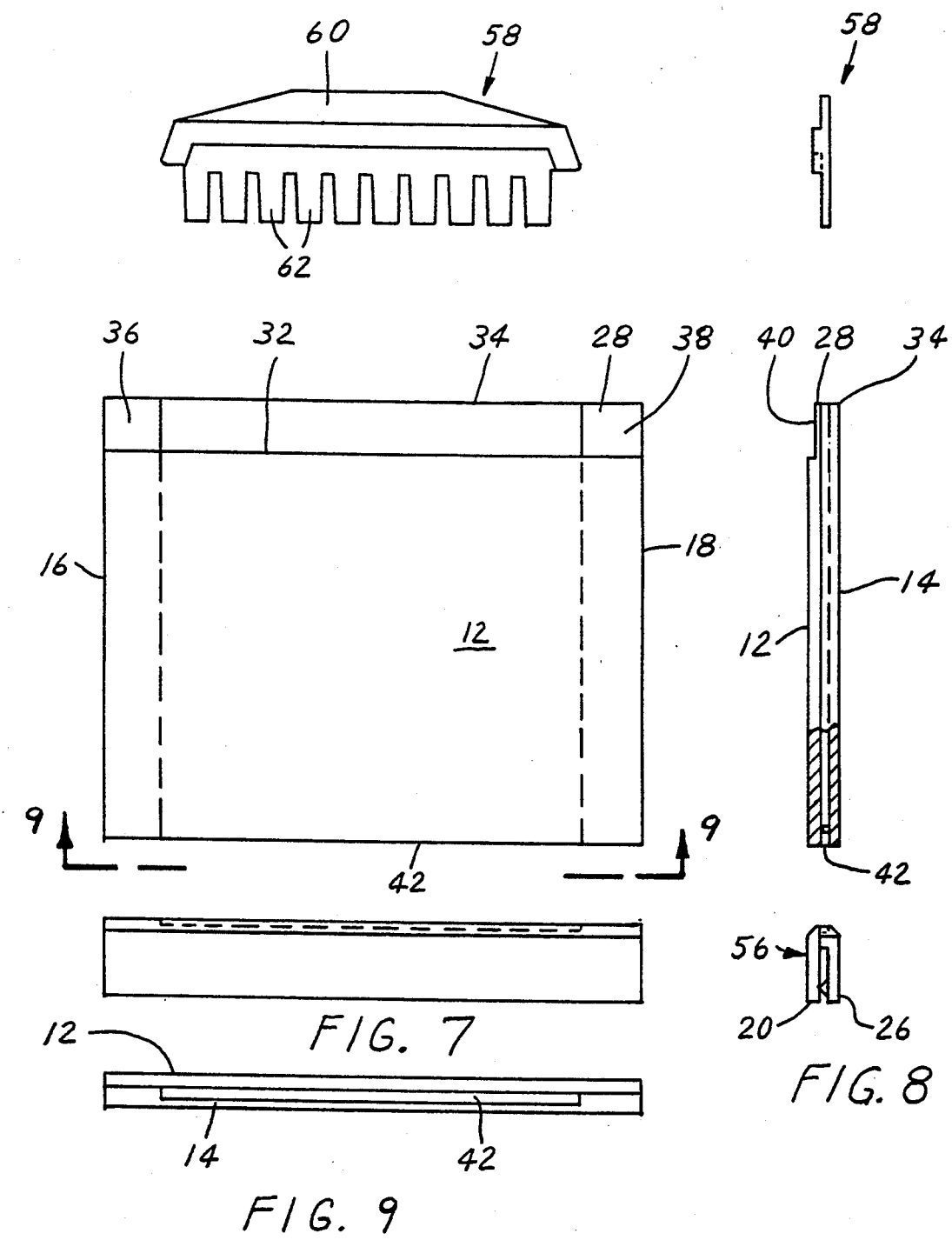

MOLDED PLASTIC ELECTROPHORESIS CASSETTES

BACKGROUND OF THE INVENTION

The present invention relates to electrophoresis cassettes made entirely of plastic materials.

Electrophoresis gels are widely used for separating and analyzing biomolecular materials such as proteins, DNA and DNA sequence, for example. A gel medium, such as agarose or acrylamide, is commonly held inside a thin, rectangular shaped cassette composed of two electrically-insulating, liquid impermeable sheets, such as glass plates, which are held in spaced apart, opposing relationship by insulating spacers or the like.

A liquid solution containing the medium is poured, pumped or pipetted into the space or gap created by the two plates in the cassette. A comb type device may be inserted into the cassette while the media is still in a liquid form. The agarose or acrylamide solutions are made to change into a gel either by cooling as in the case of agarose or via polymerization as in the case of acrylamide. The comb enables sample wells to form in the gel. The entire top of the gel may be used for separating sample, if a researcher chooses not to use a comb. After the comb is removed, samples can be loaded into each well for electrophoresis.

These cassettes are typically placed in an apparatus where electrical power is made to pass through the gel causing the biological sample to travel through the gel media. During travel of the sample material through the gel, the components of the sample separate from each other based upon principles of electrophoresis.

Originally, cassettes were made using two glass plates with a spacer material placed between the glass on each end in order to create the gap where the gel media is located. The glass plates were normally sealed on the bottom of the cassette using any of various means such as tape or silicone rubber gaskets, for example. These prior art designs, unfortunately, require extra labor and are costly to manufacture.

It has been proposed to make integral plastic cassettes that would reduce labor and material costs and which would be more economical to manufacture. However, attempts to make such plastic cassettes that are compatible with many of the existing electrophoresis apparatus have not proven altogether successful. One problem has been that in order to seal the bottom of the cassette gap without at the same time increasing the size of the cassette, it would be necessary to reduce the vertical height of the gel medium. Unfortunately, this limits the usefulness of the plastic cassette as compared to prior designs.

Another problem has been that plastic cassettes must be made thin enough to fit into existing apparatus. A front plate made of plastic is not as stiff as a glass plate of the same thickness and, consequently, thin plastic plates are more prone to excessive deflection. Deflection of the front plate can be detrimental to both the gel formation and operation.

Some prior art cassettes have been made utilizing a back plate made of plastic and a thin front plate made of glass in order to accommodate the limited space and to interface with and seal against the stepped upper tank buffer seal of some existing apparatus. These cassettes, nevertheless, utilize tape on the bottom and along the front plate of the cassette to seal the liquid contained in the gel during polymerization. The assembly of plastic and glass require additional labor and cost to manufacture.

Another prior art cassette has been made utilizing plastic front and back plates wherein a slot located on the back plate of the cassette exposes the lower portion of the gel. However, in order to employ the slot in cassettes for some existing electrophoresis apparatus, a portion of the gel length would have to be reduced. Furthermore, these slotted cassettes would require the use of tape to seal off the slots.

It is therefore an important object of the invention to provide an improved electrophoresis cassette which is made entirely of plastic material, which is economical to manufacture and which is compatible with electrophoresis apparatus currently in the field.

Another object of the invention is to provide an improved electrophoresis cassette which maintains nearly the same gel length as that produced in glass cassettes of the prior art and which are compatible with existing electrophoresis apparatus.

Still another object of the invention is to provide an improved electrophoresis cassette that will interface properly with the step type seal employed in existing electrophoresis apparatus.

SUMMARY OF THE INVENTION

The present invention is directed to an electrophoresis cassette which is made entirely of plastic material. The cassette of the invention comprises a pair of thin, flat, rectangular, molded plastic plates which overlie one another in opposing but spaced apart relation to form a gap for holding a gel medium. The plates are separated from each other by an embossment that is integrally formed on the surface of one of the plates. Preferably, the embossment takes the form of a U-shaped ridge that extends continuously along the marginal edges of the plate, except at the top of the plate. The plates are joined together preferably by an ultrasonic weld which extends continuously along the embossment, joining both plates and providing a liquid tight seal around the gap. The gap is open at the top of the cassette for introducing sample solution but is normally closed by the liquid-tight seal to prevent leakage of liquid during polymerization of the gel. An elongated narrow groove is provided within the outer surface of each plate near the bottom of the cassette. The grooves extend across the width of the plates in substantially coinciding relation at a point just above the seal and form a tab which can be broken off to expose the gel inside the gap. Once the tab is removed, the gel is exposed and it can communicate with the lower tank buffer in order to conduct electrophoresis.

The cassette of the present invention produces a gel of nearly the same length as gels made in glass for existing electrophoresis apparatus without at the same time substantially increasing the thickness of the cassette. Moreover, the cassette does not require the use of tape or other sealing devices which are labor intensive and increase cost.

The present cassette also incorporates a stepped portion which is molded into the top of the front plate along the outer side edges thereof which enables the cassette to interface properly with the step seal for the upper buffer tank in existing electrophoresis apparatus. This feature also allows the use of a thicker front plate which is more resistant to excessive deflection and provides a cassette thickness that will fit into existing electrophoresis apparatus.

BRIEF DESCRIPTION OF THE DRAWINGS

The invention will now be described in greater detail with particular reference to the accompanying drawings which show the preferred embodiments thereof and wherein:

FIG. 7 is an elevational view of the electrophoresis cassette showing the sample well-forming comb removed from the top open end of the cassette and the break-away tab broken off from the bottom of the cassette;

FIG. 8 is a side elevational view of the cassette and broken off tap shown in FIG. 7;

FIG. 9 is a bottom view of the cassette taken along the line 9—9 in FIG. 7; and

DESCRIPTION OF THE PREFERRED EMBODIMENTS

Figure 1:
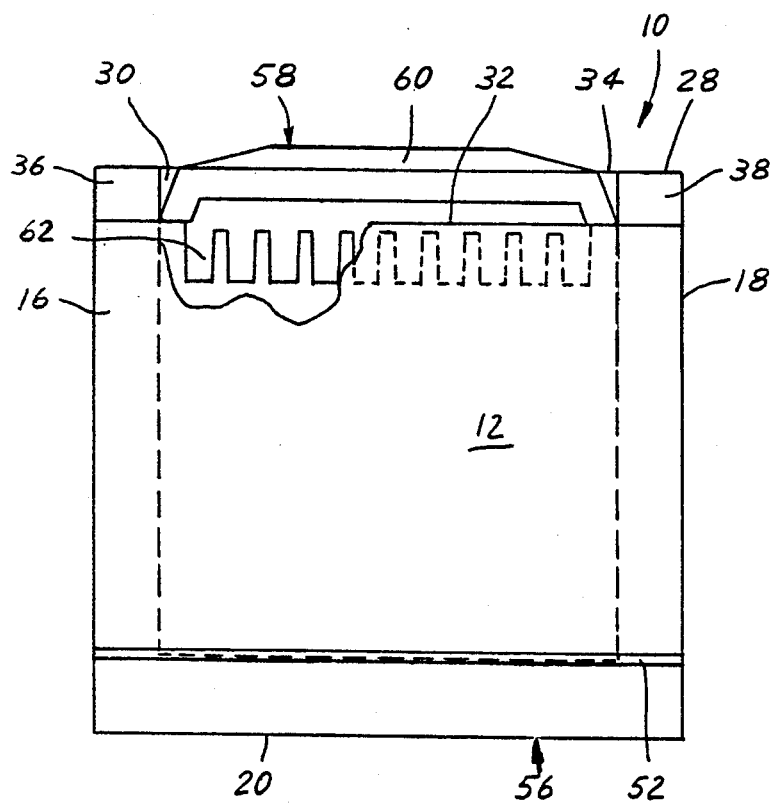
FIG. 1 is an elevational view of a molded plastic electrophoresis cassette according to the invention.
Figure 2:
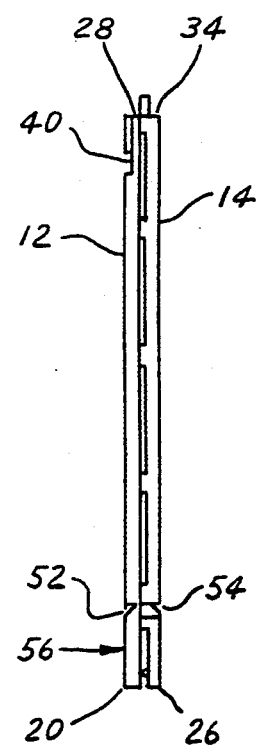
FIG. 2 is a side view of the electrophoresis cassette shown in FIG. 1.

Referring now to the drawing and particularly to FIGS. 1 and 2, there is shown an electrophoresis cassette 10 according to the invention. The cassette includes a thin, rectangular, molded plastic front plate 12 and a thin, rectangular, molded plastic back plate 14 both of which are essentially the same size, e.g., approximately 8 cm. tall by 10 cm. wide in a typical embodiment. The front and back plates 12, 14 are preferably made by injection molding a suitable plastic material such as acrylic, acrylic based plastics and polystyrene, for example.

Figures 5, 6:
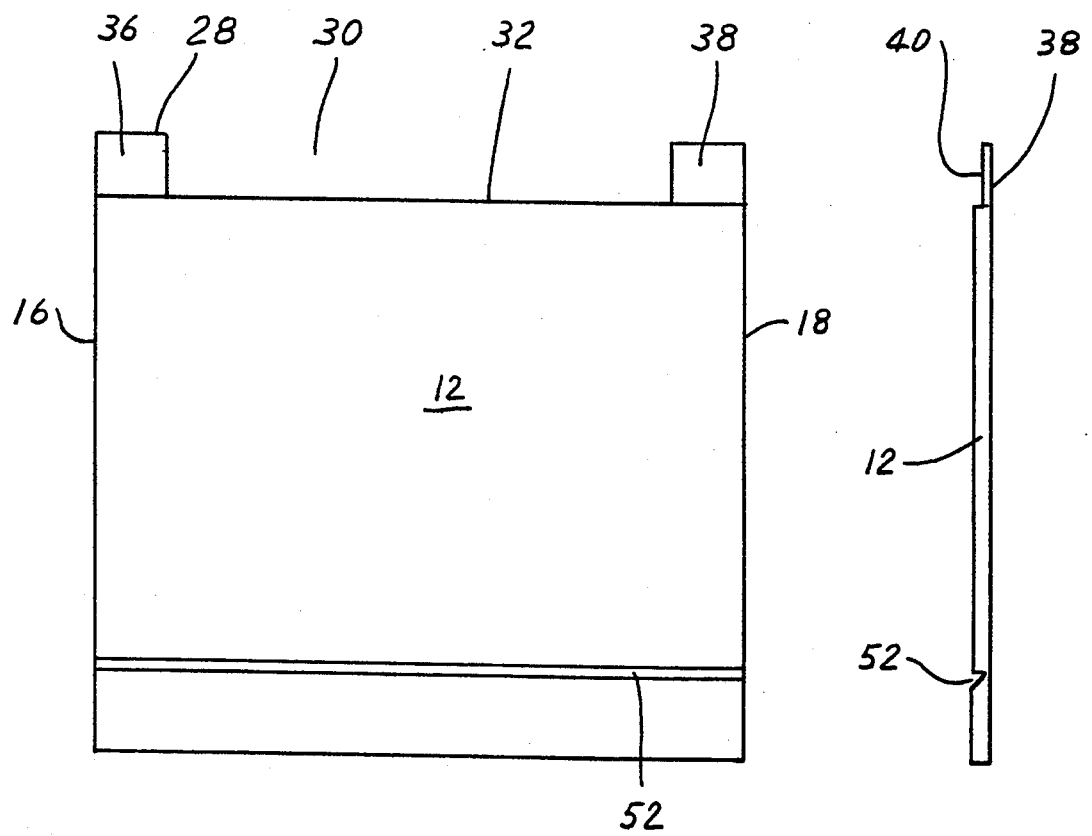
FIG. 5 is an elevational view of the molded plastic front plate used in the cassette of FIG. 1.
FIG. 6 is a side view of the front plate.

The front plate 12 overlies the back plate 14 with its two opposite side edges 16, 18 and its bottom edge 20 substantially coinciding with the respective side edges 22, 24 and the bottom edge 26 of the back plate 14 as best shown in FIG. 2. The top edge 28 of the front plate 12 is cut away as at 30 (FIG. 5) to provide a cassette opening 32. The cassette opening 32 is disposed below the top edge 34 of the back plate 14 as seen in FIG. 1.

The front plate 12 is also formed with two outer marginal extensions 36, 38 along each side edge 16, 18, respectively, which coincide with the top edge 34 of the back plate 14. These extensions or tabs are molded to a reduced thickness, say about 0.04 inch, to provide a stepped portion 40 as best shown in the view of FIG. 2. As shall be described hereinafter, the step portion 40 at the top edge of the front wall 12 accommodates the stepped seal for the upper buffer tank in existing electrophoresis apparatus.

Figures 3, 4:
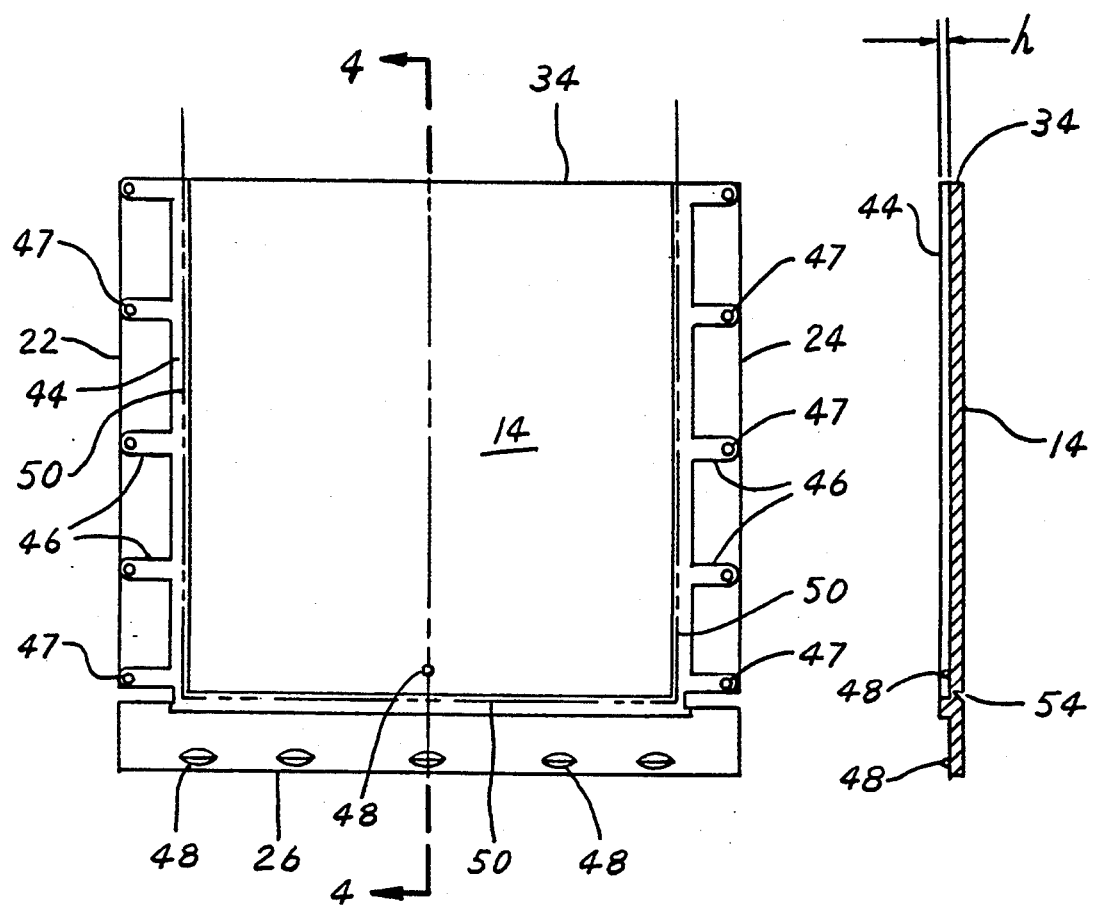
FIG. 3 is an elevational view of the molded plastic back plate used in the cassette of FIG. 1.
FIG. 4 is a sectional view of the back plate taken along the line 4—4 in FIG. 3.

As shown in FIG. 3, the back plate 14 is integrally formed with an embossment on its surface facing the front plate 12 for spacing the two plates apart a fixed distance sufficient to provide a gap 42 for the gel medium (see FIG. 9). In the embodiment of the cassette illustrated, the embossment is an elongated, narrow, substantially flat, generally U-shaped ridge 44. The ridge 44 extends continuously from the top edge 34 of the back plate 14 down along the left side edge 22, across the bottom portion of the plate 14 and then upwardly along the right side edge 24 to the top edge 34 of the plate.

Preferably, the embossed ridge 44 is spaced a short distance above the bottom edge 26 of the plate 14 as shown in FIG. 3. The ridge 44 is also preferably spaced a short distance inwardly from the opposite side edges 22, 24 of the plate 14. As best shown in FIG. 4, the ridge 44 protrudes slightly above the flat planar surface of the back plate 14 a fixed distance or height "h" which determines the width of the gap 42.

The back plate 14 may also be provided with a number of other embossments in addition to the ridge 44 to strengthen the cassette. Thus a series of ribs 46 may be formed which extend outwardly from the ridge 44 at spaced apart points along both side edges 22, 24 of the plate 14. The ribs 46 may also be formed with adjacent circular pads 47 which help to prevent bowing of the plates when the cassette is placed in some existing electrophoresis apparatus. In addition, a plurality of circular nibs 48 may be molded at spaced points along the bottom of the plate 14 to strengthen the cassette.

The cassette 10 is assembled by securing the front plate 12 to the back plate 14 along the U-shaped spacer ridge 44 preferably by ultrasonic welding. The energy director for forming the continuous ultrasonic weld along the ridge 44 is depicted at 50 in FIG. 3. The weld joins the two plates 12, 14 together and seals off the gap 42 against leakage of liquid during formation of the gel medium.

Preferably, the front plate 12 is also ultrasonically welded to the series of ribs 46, circular pads 47 and the nibs 48 on the back plate 14, offering added strength to the cassette 10. It should be noted that the ribs 46 are integrally molded with the back plate 14 and protrude approximately to the same height as the spacer ridge 44. The circular pads 47 and the nibs 48 are also integral with the plate 14 but protrude approximately to the height of the energy director and melt down to the level of the ridge 44 during welding. Once assembled, the cassette is typically about 0.5 cm. thick. It should also be noted that the weld provides a water-tight seal but the weld strength is weak enough to permit prying open of the two cassettes halves after electrophoresis of the sample.

An elongated, narrow, V-shaped groove 52 is provided within the outer surface of the front plate 12 as best seen in FIGS. 1 and 2. The groove 52 extends completely across the surface of the plate 12 at a point just above the ultrasonic weld 50. Similarly, an elongated, narrow, V-shaped groove 54 is provided within the outer surface of the back plate 14 as best seen in FIG. 4. This groove 54 also extends completely across the surface of the plate 14 at a point just above the ultrasonic weld 50 and coincides with the groove 52. The two grooves 52, 54 substantially weaken the plates 12, 14 at the bottom of the cassette and provide a tab 56 which can be easily broken off to expose the gel medium.

As probably best seen in FIGS. 1 and 2, the tab 56 extends across the entire width of the cassette 10 providing mechanical leverage to break off the bottom of the cassette where the ultrasonic seal is located. Since both of the grooves 52, 54 are positioned above the seal, the entire bottom edge of the gel is exposed when the tab 56 is broken off at the bottom of the cassette 10.

FIGS. 7-8 show the cassette 10 after the tab 56 has been removed. It will be noted particularly that while the cassette 10 has been totally protected against leakage by the ultrasonic seal during formation of the gel, once the seal is broken by removing the tab 56, the vertical height of the gel will remain essentially the same as that employed in prior cassettes.

There is ease of manufacturing precast gels with the cassette of the invention because liquid media can be placed into the cassette without the need for adhesive tape to seal the bottom of the cassette or a slot on the side of the cassette. These prior art cassettes require extra labor especially those made from two glass plates and are more expensive to manufacture. They are also not compatible with some electrophoresis apparatus.

Although not a part of the present invention, a comb 58 is shown inserted within the cassette opening 32 for forming a plurality of sample wells on top of the gel. The comb 58 consists of a handle portion 60 and a number of depending fingers 62 which protrude into the gel and form the sample wells.

Figure 10:
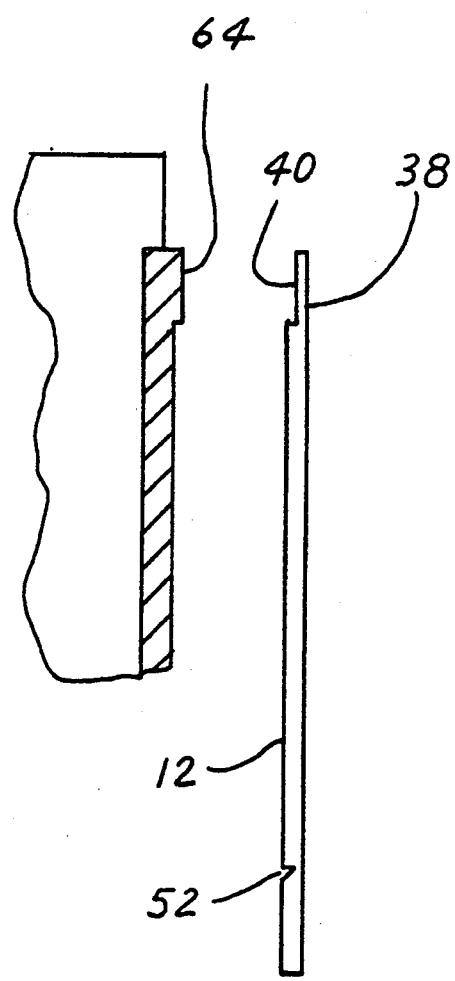
FIG. 10 is a fragmentary view of part of an electrophoresis apparatus showing the tab that mounts flush against the step seal for the upper buffer tank in certain apparatus and the front plate of the cassette of FIG. 1.

The cassette of the present invention employs a front plastic plate 12 that is designed specifically to interface with the stepped seal for the upper buffer tank in an existing electrophoresis apparatus. This feature is best illustrated in FIG. 10 wherein the stepped seal 64 on the buffer tank is shown together with the top portion of the front plastic plate 12. The front plate 12 is shown in position just prior to assembly with one of the marginal extensions 38 at the top edge of the plate spaced opposite to the seal 64. It will be seen that the stepped portion 40 on the plate 12 is of such a configuration and size as to interface easily with the stepped seal 64 and provide a good liquid-tight seal in the electrophoresis apparatus.

Instead of a glass plate, it will also be noted that the front plate design illustrated in FIG. 10 enables the use of a sufficiently thick plate which can be readily manufactured by injection molding. In addition, the thicker plastic plate would be as stiff as plates made of glass in prior cassettes and would prevent excessive deflection. Furthermore, by incorporating the marginal extensions 36, 38 at the top of the plate 12, it is possible to employ two plastic cassette halves that could be ultrasonically welded together on three sides with the ultrasonic weld extending the entire distance to the top of the cassette.

Thus the invention provides an electrophoresis cassette wherein the bottom and the two side edges of the cassette are sealed to prevent leakage of the gel media when the gel is in a liquid form. Gel solutions are generally poured into the cassette when the cassettes are placed in a vertical position, however, the cassettes may be placed at any angle as long as the media does not leak out. These cassettes may be used for single concentrations of solutions or for gradient solutions, where the concentration of media changes from the top of the cassette to the bottom.

Cassettes of the invention can be molded using plastic material that is transparent to a segment of the range of ultraviolet (UV) light. Unlike glass, a UV transparent plastic offers certain advantages. For the visualization of DNA after electrophoresis, researchers currently use ethidium bromide as a intercalating agent which binds to the DNA sample to be separated. The ethidium bromide can be incorporated into the gel solution prior to polymerization, mixed with the DNA sample prior to loading or used to stain the gel after electrophoresis. The sample is separated in the gel and in order to see and photograph the sample, the gel must be viewed under UV light. The ethidium bromide bound to the DNA will fluoresce, that is, it will give off light when it is exposed to UV light.

If the ethidiun bromide is incorporated into the sample prior to loading, the gel is removed manually from between two glass plates before viewing under UV light because glass will filter out or prevent UV light from passing. This causes two problems: first, the researcher runs the risk of contacting the ethidium bromide which is known as a very powerful carcinogen/mutagen; second, in the process of opening the glass cassette containing the gel, the gel could tear or be damaged. Although it would be beneficial to run thinner gels to achieve shorter run times, it is currently necessary to pour gels of reasonable thickness so they can be handled without damage.

If the researcher stains the gel with ethidium bromide after running the gel, again there is the risk factor involved with contacting the ethidium bromide while staining and destaining.

In order to minimize exposure to ethidium bromide and to have thinner gels that would run quicker, it is desirable to have a cassette that would not have to be opened for viewing under UV light. Cassettes made of a UV transparent plastic would provide an important improvement to the current state of the art. The gel solution would be poured in the plastic cassette with ethidium bromide already incorporated. The researcher would simply load the sample, run the gel, and then carry the plastic cassette to a UV source for viewing and/or photographing. Since the cassette could be viewed under UV light without opening the cassette, researchers would minimize their exposure to ethidium bromide and be able to utilize thinner faster running gels which would save considerable time.

The plastic material should be sufficiently transparent to UV light that it will fluoresce the ethidium bromide or other intercalating agent enough to view the sample. Ethidium bromide fluoresces when excited by ultraviolet light in the range of approximately 280 to 360 nanometers (nm). Certain acrylics and nylons, for example, are available which will transmitt at least 50% of UV light within this range of wavelengths and are sufficient for viewing the sample.

A number of modifications can be made to the electrophoresis cassette described herein without departing from the spirit of the invention. For example, it is possible to employ the embossments including the U-shaped ridge, ribs, circular pads and nibs or any combination thereof within the front plate instead of the back plate. Also, the marginal extensions or tabs located at the top edge of the front plate need not be stepped or reduced in thickness to accommodate the seal at the upper buffer tank of some existing electrophoresis apparatus and can be made flush with the front plate if desired.

What is claimed is:

1. An electrophoresis cassette comprising, in combination: a pair of thin, flat, rectangular, molded plastic plates overlying one another in opposing relationship, said plates being separated from each other by an embossment formed on one of said plates, said embossment extending continuously along the marginal edges of said one of said plates except at the top edge thereof; a liquid-tight seal extending along said embossment and joining said plates together, said plates defining therebetween a narrow gap for holding a gel medium, said plates having elongated narrow grooves within the non-opposing surfaces thereof extending in substantially coinciding relation across the bottom of said plates at a point just above said seal, said grooves being of sufficient depth so as to substantially weaken said plates along the length of said grooves whereby the bottom of said plates can be easily broken off to expose said gap.

2. An electrophoresis cassette according to claim 1 wherein said liquid-tight seal is an ultrasonic weld.

3. An electrophoresis cassette according to claim 2 wherein said embossment is a thin, narrow, generally U-shaped ridge extending along the two opposite side edges and the bottom edge of said one of said plates.

4. An electrophoresis cassette according to claim 3 wherein a series of ribs are formed along with said U-shaped ridge extending outwardly from said ridge toward said opposite side edges of said one of said plates to add strength to said cassette.

5. An electrophoresis cassette according to claim 4 wherein a plurality of circular pads are formed along with said ribs to prevent bowing of said plates.

6. An electrophoresis cassette according to claim 5 wherein a plurality of nibs are formed at spaced apart points along said bottom edge of said one of said plates to add strength to said cassette.

7. An electrophoresis cassette according to claim 6 wherein the other of said plates is cut away at its top edge leaving a pair of marginal extensions along the opposite side edges thereof, said marginal extensions being joined to said side edges of said one of said plates by said ultrasonic weld.

8. An electrophoresis cassette according to claim 7 wherein the thickness of said marginal extensions is less than the thickness of said other plate forming a stepped portion at the top of said cassette.

9. An electrophoresis cassette according to claim 8 wherein at least one of said plates is made of a plastic material which is substantially transparent to ultraviolet light.

10. An electrophoresis cassette comprising, in combination: a thin, flat, rectangular, molded plastic front plate overlying a thin, flat, rectangular, molded plastic back plate in opposing spaced apart relationship, said front and back plates being separated from each other by a thin, narrow, generally U-shaped ridge formed on the opposing surface of said back plate and extending along the two opposite side edges and the bottom edge of said back plate; a liquid-tight seal extending continuously along said ridge and joining said plates together, said plates defining therebetween a narrow gap for holding a gel medium, said plates having elongated narrow grooves within the non-opposing surfaces thereof extending in substantially coinciding relation across the bottom of said plates at a point just above said seal, said grooves forming at the bottom portion of said plates a tab which can be easily broken off to expose the bottom of said gel within said gap.

11. An electrophoresis cassette according to claim 10 wherein said liquid-tight seal is an ultrasonic weld.

12. An electrophoresis cassette according to claim 11 wherein said front plate is cut away at its top edge leaving a pair of marginal extensions along the opposite edges thereof, said marginal extensions having a thickness which is less than the thickness of said front plate forming a stepped portion at the top of said front plate, said marginal extentions being joined to the side edges of said back plate by said ultrasonic weld.

13. An electrophoresis cassette comprising, in combination: a pair of thin, flat, rectangular, molded plastic plates overlying one another in opposing relationship, said plates being separated from each other by a continuous liquid-tight seal extending along the marginal edges of said plates, except at the top edge thereof, joining said plates together and defining therebetween a narrow gap for holding a gel medium, said plates having elongated narrow grooves within the surfaces thereof extending in substantially coinciding relation across the bottom of said plates at a point just above said seal, said grooves being of sufficient depth so as to substantially weaken said plates along the length of said grooves whereby the bottom of said plates can be easily broken off to expose said gap.

14. An electrophoresis cassette comprising, in combination: a pair of thin, flat, rectangular, molded plastic plates overlying one another in opposing spaced apart relationship; a continuous liquid-tight seal extending along the marginal edge portions of said plates, including the bottom thereof, joining said plates together and defining therebetween a narrow gap for holding a gel medium, said gel medium containing ethidium bromide as an intercalating agent, at least one of said plates being composed of a plastic material which will transmit at least 50 percent of ultraviolet light within a range of wavelengths of from about 280 to about 360 nanometers.

15. An electrophoresis cassette according to claim 14 wherein said plastic material is selected from the group consisting of acrylics and nylon.

* * * * *